United States Patent
Chen et al.

(10) Patent No.: US 9,642,731 B2
(45) Date of Patent: May 9, 2017

(54) DEGRADABLE POLYESTER STENT AND PREPARATION METHOD THEREOF

(71) Applicant: SHANGHAI MICROPORT MEDICAL (GROUP) CO., LTD., Shanghai (CN)

(72) Inventors: Shuguo Chen, Shanghai (CN); Juan Meng, Shanghai (CN); Baoai Chen, Shanghai (CN); Qiyi Luo, Shanghai (CN)

(73) Assignee: SHANGHAI MICROPORT MEDICAL (GROUP) CO., LTD., Shanghai (CN)

( * ) Notice: Subject to any disclaimer, the term of this patent is extended or adjusted under 35 U.S.C. 154(b) by 0 days.

(21) Appl. No.: 14/654,437

(22) PCT Filed: Dec. 20, 2013

(86) PCT No.: PCT/CN2013/090112
§ 371 (c)(1),
(2) Date: Jun. 19, 2015

(87) PCT Pub. No.: WO2014/094655
PCT Pub. Date: Jun. 26, 2014

(65) Prior Publication Data
US 2015/0328024 A1 Nov. 19, 2015

(30) Foreign Application Priority Data
Dec. 21, 2012 (CN) .......................... 2012 1 0563424

(51) Int. Cl.
*A61F 2/06* (2013.01)
*A61F 2/90* (2013.01)
(Continued)

(52) U.S. Cl.
CPC ................ *A61F 2/90* (2013.01); *A61L 31/06* (2013.01); *A61L 31/128* (2013.01); *C08L 67/04* (2013.01); *Y10T 29/49828* (2015.01)

(58) Field of Classification Search
CPC ...... A61F 2/06; A61F 2/82; A61F 2/91; A61F 2/90
See application file for complete search history.

(56) References Cited

U.S. PATENT DOCUMENTS

2003/0190418 A1 10/2003 Tseng
2006/0118122 A1 6/2006 Martens et al.
(Continued)

FOREIGN PATENT DOCUMENTS

| CN | 101991881 A | 3/2011 |
| CN | 102198294 A | 9/2011 |

(Continued)

OTHER PUBLICATIONS

Office Action of priority No. 201210563424.X dated Dec. 31, 2014 (pp. 1-4).

*Primary Examiner* — Jason-Dennis Stewart
(74) *Attorney, Agent, or Firm* — Muncy, Geissler, Olds & Lowe, P.C.

(57) ABSTRACT

A degradable polyester stent is disclosed, which includes a polyester composite, wherein the polyester composite is produced from a biodegradable polyester and a metal-based material. A method of preparing the degradable polyester stent is also disclosed. The method can improve the mechanical properties of the biodegradable copolymer stent and can achieve the radiopacity of the main body and the overall of the stent.

7 Claims, 1 Drawing Sheet

(51) Int. Cl.
*A61F 2/82* (2013.01)
*C08L 67/04* (2006.01)
*A61L 31/06* (2006.01)
*A61L 31/12* (2006.01)

(56) References Cited

U.S. PATENT DOCUMENTS

| | | | |
|---|---|---|---|
| 2008/0082162 A1* | 4/2008 | Boismier | A61F 2/91 623/1.38 |
| 2009/0149940 A1 | 6/2009 | Wang et al. | |
| 2009/0240323 A1 | 9/2009 | Wilcox | |
| 2009/0254171 A1* | 10/2009 | Heikkila | A01K 95/005 623/1.15 |
| 2010/0087910 A1* | 4/2010 | Weber | A61L 31/022 623/1.15 |
| 2011/0015726 A1 | 1/2011 | Wang et al. | |
| 2011/0130822 A1* | 6/2011 | Cottone | A61F 2/91 623/1.15 |
| 2012/0053674 A1* | 3/2012 | Boismier | A61F 2/91 623/1.15 |

FOREIGN PATENT DOCUMENTS

| | | |
|---|---|---|
| CN | 102397589 A | 4/2012 |
| CN | 102504508 A | 6/2012 |
| CN | 102532835 A | 7/2012 |

\* cited by examiner

DEGRADABLE POLYESTER STENT AND PREPARATION METHOD THEREOF

TECHNICAL FIELD

The present invention pertains to the field of medical instruments and, more particularly, relates to a degradable polyester stent and preparation method thereof.

BACKGROUND

As important instruments for the treatment of stenosis, stents have found increasingly extensive use in the field of cardiovascular diseases. Metal stents, that are widely used in the contemporary clinical practices, will permanently exist in the body after the fulfillment of their therapeutic mission, and are thus associated with a number of drawbacks such as, for example, deteriorating coronary MRI or CT images, hindering surgical revascularization, impeding collateral circulation and inhibiting positive vessel remodeling. Biodegradable stents have aroused widespread attention as a possible alternative solution.

A biodegradable stent is fabricated from a degradable polymeric or metallic material, and after its deployment to a treatment site, the biodegradable stent can support a vessel for a limited period of time to allow revascularization thereof. After the treatment regimen, the biodegradable stent will degrade in the body into absorbable or metabolizable organic substances and eventually disappear.

Biodegradable polymeric materials commonly used for fabricating such stents include polylactic acid (PLA), polyglycolic acid (PGA) and polycaprolactone (PCL), and biodegradable metallic materials commonly used for fabricating such stents include magnesium alloys and iron-based alloys. Magnesium and iron are essential trace elements in living organisms, which have good biocompatibility, unique degradation and absorption properties, excellent mechanical properties and molding properties.

However, it is found in practical use that, polymer stents generally have poorer mechanical properties and larger sizes compared with metal stents, and are more likely to induce vascular lumen loss, local inflammation and intimal hyperplasia. Moreover, polymer stents are not radiopaque. On the other hand, magnesium alloys stents have been found degrading too fast, which results in a too fast decay of the mechanical strength of magnesium alloys stents in the body and the effect of treatment is affected. Although the mechanical property of iron-based alloy stent meets the requirement, the corrosion rate of iron-based alloy stent is difficult to control, and the corrosion degradation mechanisms in the simulated body fluid and human environment are unknown, thus limiting the application of iron-based alloy stent as cardiovascular stent.

In order to overcome the problem of too fast degradation of magnesium alloys stents, U.S. Patent Publication No. US2009240323A1 describes a method of coating a biodegradable polymer on the surface of magnesium stent which can realize controllable degradation of magnesium stent. However, the polymer coating is required to be dense enough to prevent the body fluid from permeating through the biodegradable polymer coating into the magnesium stent to cause the degradation of the magnesium stent.

In order to solve the problem of weak mechanical properties of biodegradable polymer stents, U.S. Patent Publication No. US20110015726 describes a method of improving the mechanical properties of biodegradable stents which uses ceramic materials serving as reinforcing materials to add in biodegradable materials. However, the degradation mechanism of ceramic material in blood is not clear, and toughness of the material will be significantly decreased. Another U.S. Patent Publication No. US2009248147A1 describes a method of improving the mechanical properties of biodegradable copolymer stents which uses homopolymer and inorganic salt as nucleating agents to add in biodegradable copolymer materials. But the crystallization rate of the copolymer itself is lower than that of the homopolymer, and therefore the mechanical strength of the stent is not significantly improved by the addition of nucleating agent.

In order to solve the radiopacity problem, U.S. patent publication No. US2009149940A1 disclosed a method of coating a radiopaque layer with radiopaque particles on the surface of a stent to achieve the overall radiopacity of the stent. However, the mechanical strength of the radiopaque layer is relatively low, and the radiopaque efficiency is relatively poor. The coating may also have the defect of bonding too tight with the main body of the stent.

In addition, Chinese patent publication No. CN102532835A disclosed a method of casting molding a stent using a composite prepared by solution blending polylactic acid and magnesium. This method uses magnesium as an inorganic medium to improve the mechanical properties of PLA stent, and to neutralize the acidic substances produced from the degradation of PLA. However, due to the strength of magnesium is not much higher than PLA, and both have poor interface compatibilities, therefore, the improvement of the mechanical properties is limited. Further, the method fails to effectively utilize the crystallization properties of PLA, resulting in a relatively low mechanical strength of the stent.

Thus, there is still a need for a biodegradable stent having a better performance in the prior art.

SUMMARY OF THE INVENTION

The present invention provides a degradable polyester stent and a preparation method thereof, wherein the polyester matrix is blended with degradable metal-based powders, which not only improves the crystallization properties of the polyester material, but also serves as reinforcing agents to improve the mechanical properties of the stent. Metal ions released from the degradable metal material can prevent or inhibit the occurrence of vascular restenosis. Moreover, some biodegradable metals may also be radiopaque and traceable, thus improving the radiopacity of the polyester stent.

In particular, the present invention relates to a degradable polyester stent, including a polyester composite, wherein the polyester composite is produced from a biodegradable polyester and a metal-based material, wherein the metal-based material is in the form of powders.

According to the invention, the biodegradable polyester includes, but not limited to, one or more of the following materials: polylactic acid (PLA), polyglycolic acid (PGA), poly(L-lactide-co-glycolide) (PLGA), polycaprolactone (PCL), poly(trimethylene carbonate) (PTMC), polyesteramide, polybutylene succinate) (PBS), poly(hydroxybutyrate-hydroxyvalerate) (PHBV), polyacetylglutamic acid, polyorthoesters (POE), and other polyester materials.

According to the invention, the metal-based material includes, but not limited to, one or more of the following materials: pure magnesium, pure iron, magnesium-based alloy, magnesium salt, iron-based alloy and so on; wherein, the iron-based materials can improve the radiopacity of the stent.

According to the invention, the metal-based material constitutes 0.1% to 20% by weight of the polyester composite, and the biodegradable polyester constitutes the remaining of the polyester composite.

According to the invention, the metal-based material has a powder diameter of between 10 nm and 10 µm.

The present invention also relates to a method of preparing degradable polyester stent, which includes dispersing metal-based material into a polyester matrix to prepare a polyester composite, and subjecting the polyester composite to extrusion molding, post-treatment and cutting processes to form a stent. The method specifically includes the steps of:

preparing a polyester composite by adding metal-based powders into a polyester matrix through solution blending, melt blending or mechanical blending;

in order to make the metal-based powders uniformly dispersed in the polyester matrix and to improve the compatibility between the powders and the polyester matrix, preferably, the metal-based powders may be subjected to a surface modifying treatment, for example be modified with hydroxyl groups, be grafted with organic functional groups, and so on;

molding the polyester composite into a tube by screw extrusion at a temperature higher than a melting temperature of the polyester composite, wherein, the metal-based material is used as a reinforcing medium to improve the mechanical properties of polyester material;

cutting the tube into a stent with or without a treatment step, the treatment including any one of annealing, inflating and stretching, or combinations thereof. The purpose of the treatment is to further improve the strength, toughness and crystallinity of the tube.

In order to improve the crystallinity of the tube, the treatment is performed at a temperature between a glass transition temperature and a melting temperature of the polyester.

The present invention is different from the prior art in the composition of the polyester composite, the preparation method of the stent and the characteristics of the stent. The method of the present invention can improve the crystallization ability of the degradable polyester, and hence improve the mechanical properties of the polyester and the stent. The stent provided by the present invention has a simple fabrication process, and can be easily produced with a large yield. The stent of the present invention has excellent biocompatibility. Some stents may have good radiopacity and hence can achieve the radiopacity of the main body and the overall of the stent.

BRIEF DESCRIPTION OF THE DRAWINGS

In order that the subject matter of embodiments of the present invention may be more clearly understood, brief description of the accompanying drawings that are referenced in the description of the embodiments is set forth below. It is apparent that the drawings described below are merely several specific embodiments provided in this application and are not intended for limiting the scope of protection of the invention. It is of course that those skilled in the art can make other embodiments and drawings without exerting creative efforts based on the embodiments and drawings disclosed herein.

DETAILED DESCRIPTION

Figure 1:
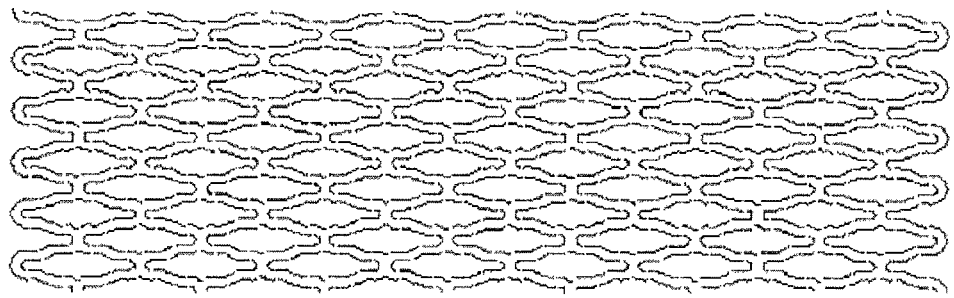
FIG. 1 depicts a resulting stent constructed in accordance with the present invention.
Figure 2:
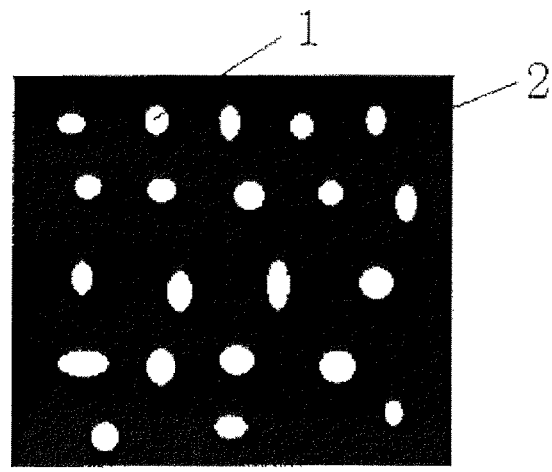
FIG. 2 depicts the metal particles evenly distributed in the polyester matrix, wherein 1 represents metal particles, 2 represents polyester matrix.

In order to better understand the invention, the preferred embodiments of the present invention will be described below with reference to the following examples. These descriptions are only examples of the characteristics and advantages of the biodegradable polyester stent of the present invention, rather than limiting the protection scope of the present invention

EXAMPLE 1

Adding a certain amount of nano iron powders (4-8 g, particle size smaller than 10 µm) into 500~1000 ml of dichloromethane solution, stirring and performing an ultrasonic treatment on the solution to make nano iron powders to be uniformly dispersed in the solution; further adding 96~192 g of Poly(L-lactic acid) particles having weight-average molecular weight of 300 thousand therein; after being completely dissolved and evenly stirred, freeze drying the solution and crush into particles to obtain PLA/iron composite material, wherein the nano iron powders constituted 4% by weight of the composite material.

PLA/iron composite material was single-screw extruded to form a tube having an outer diameter of 1.8 mm and an inner diameter of 0.5 mm. The tube had a tensile strength of 70 MPa and an elastic modulus of 2.5 GPa, which was higher than a PLA tube of the same size.

Subsequently, the tube was heated to 70° C. to get an inflated tube having an outer diameter of 3.30 mm and an inner diameter of 3.05 mm.

The formed tube was laser cut into a stent and was crimped onto a balloon of a conveying system. The tube had a radial compressive strength of 150 kPa and a degree of crystallinity of 54%, which was higher than a PLA tube of the same size.

A sterilization was performed on the stent after packaging. In surgery, the stent was deployed in a vascular stenosis by the conveying system. The balloon was filled and pressurized to expand the stent, thus holding a lumen of the stenosis open. No obvious inflammatory reaction was observed after implantation. After implantation for 6 months, vascular endothelial was observed and the stent was completely degraded after implantation for 2 years.

During the operation, we can see the clear outline of the whole stent by the X-ray machine. After implantation for one week, the radiopacity of the stent was obviously lowered and the stent was blurred under the X-rays. After implantation for one month, the stent was no longer radiopaque in the X-ray machine, which means that the radiopaque material in the stent was already metabolized. During the one month, no obvious inflammatory reaction was observed. After implantation of the stent for 6 months, vascular endothelial was observed, and some corrugated struts were encapsulated by vascular endothelial cells. At this point, the inner wall of the stent was degraded, and there was no negative influence on the endothelial cells.

EXAMPLE 2

Blending and processing 100 g of magnesium oxide powders (particle size smaller than or equal to 100 nm) and 900 g of polyglycolic acid (weight-average molecular weight of 400 thousand) at the temperature of 180-220° C. by twin-screw extruder to obtain polyglycolic acid/magnesium oxide composite tube, in which magnesium alloy constituted 10% by weight of the composite material. The tube had an outer diameter of 2.8 mm and an inner diameter of 2.5 mm. The tube was annealed for 1 hour at the temperature of 120° C. to make the tube have a tensile strength of 70 MPa and an elastic modulus of 3.5 GPa, which was higher than polyglycolic acid tube of the same size.

The formed tube was laser cut into a stent and was crimped onto a balloon of a conveying system. The tube had a radial compressive strength of 120 kPa and a degree of crystallinity of 63%, which was higher than a polyglycolic acid tube of the same size.

A sterilization was performed on the stent after packaging. In surgery, the stent was deployed in a vascular stenosis by the conveying system. The balloon was filled and pressurized to expand the stent, thus holding a lumen of the stenosis open. No obvious inflammatory reaction was observed after implantation. After implantation for 6 months, vascular endothelial was observed and the stent was completely degraded after implantation for 1 year.

Compared with the prior art, the present invention has the following advantages and effects:

1) the metal-based material is dispersed in the polyester matrix, the mechanical properties of the polyester material are improved, and the mechanical strength of the polyester stent is improved;

2) metal-based material is uniformly dispersed in the polyester matrix and is served as a nucleating agent in process of inflating the polyester tube, the crystallization ability of the polyester material is improved, the degradation time of the polyester material is prolonged and the mechanical properties of the polyester material are improved;

3) during the degradation of the polyester stent, the magnesium ions produced by magnesium degradation can inhibit the inflammatory reaction during the degradation of the polyester, and further prevent the vascular restenosis;

4) during the degradation of the polyester stent, the released iron ions can reduce the proliferation of vascular smooth muscle cells by affecting the expression of the related gene, and further compete the vascular restenosis;

5) the radiopacity of the polyester stent is improved by the iron alloy material in the polyester stent, and the polyester stent has radiopacity under the X-rays;

6) the metal particles can disperse the stress in the stent and improve the fatigue life of the stent. The enhanced polyester has a high modulus and a low compliance, which can effectively reduce the creep deformation after implanting the stent in vessels.

The embodiments mentioned above are just used to help to understand the core ideas of the present invention. It is noted that although various combinations of, or modifications and variations to, the embodiments disclosed herein may be made by those of ordinary skill in the art without departing from the principles and concepts of the invention according to this application, all of these combinations, modifications and variations are considered to be also within the scope of protection of this application and in accordance with the inventive concepts.

The invention claimed is:

1. A degradable polyester stent, comprising:
   a polyester composite,
   wherein the polyester composite is produced from a biodegradable polyester and a metal-based material,
   wherein the metal-based material comprises metal-based powders uniformly dispersed in the biodegradable polyester to improve crystallization ability of the biodegradable polyester, and
   wherein the metal-based material has a powder diameter of between 10 nm and 10 μm.

2. The degradable polyester stent of claim 1, wherein the biodegradable polyester is one or more selected from polylactic acid (PLA), polyglycolic acid (PGA), poly(L-lactide-co-glycolide) (PLGA), polycaprolactone (PCL), poly(trimethylene carbonate) (PTMC), polyesteramide, poly(butylene succinate) (PBS), poly(hydroxybutyrate-hydroxyvalerate) (PHBV), polyacetylglutamic acid and polyorthoesters (POE).

3. The degradable polyester stent of claim 1, wherein the metal-based material is one or more selected from pure magnesium, pure iron, magnesium-based alloy, magnesium salt and iron-based alloy.

4. The degradable polyester stent of claim 3, wherein the metal-based material constitutes 0.1% to 20% by weight of the polyester composite, and the biodegradable polyester constitutes the remaining of the polyester composite.

5. A method of preparing a degradable polyester stent, comprising the steps of:
   preparing a polyester composite by uniformly dispersing metal-based powders in a polyester matrix through solution blending, melt blending or mechanical blending to improve crystallization ability of the polyester matrix, wherein the metal-based material has a powder diameter of between 10 nm and 10 μm;
   molding the polyester composite into a tube by screw extrusion at a temperature higher than a melting temperature of the polyester composite; and
   cutting the tube into a stent with a treatment step, the treatment comprising any one of annealing, inflating and stretching, or combinations thereof.

6. The method of claim 5, further comprising surface modifying the metal-based powders, for example with hydroxyl groups and/or organic functional groups.

7. The method of claim 5, wherein the treatment is performed at a temperature between a glass transition temperature and a melting temperature of the polyester.

* * * * *